United States Patent [19]

Friemel et al.

[11] Patent Number: 4,932,155

[45] Date of Patent: Jun. 12, 1990

[54] FUMIGANT APPLICATOR

[75] Inventors: Wolfgang Friemel, Heppenheim; Volker E. Barth, Ludwigshafen, both of Fed. Rep. of Germany

[73] Assignee: Detia Freyberg GmbH, Laudenbach, Fed. Rep. of Germany

[21] Appl. No.: 198,742

[22] Filed: May 25, 1988

[30] Foreign Application Priority Data

May 26, 1987 [ZA] South Africa .................. 87/3761

[51] Int. Cl.$^5$ .......................................... A01M 13/00
[52] U.S. Cl. .................................... 43/125; 43/131; 43/132.1; 428/34.3; 428/35.2; 428/35.7; 428/36.1; 428/76; 428/198; 428/286; 428/288; 428/290; 428/302; 428/311.1
[58] Field of Search .................. 428/34.3, 35.2, 35.7, 428/36.1, 76, 198, 286, 288, 290, 302, 311.1; 43/125, 131, 132.1; 206/484.1, 484.2, 524.2, 811; 220/417, 449, 453, 457, DIG. 11; 229/68 R, 75, 3.1, 3.5 R

[56] References Cited

U.S. PATENT DOCUMENTS

| | | |
|---|---|---|
| 4,215,508 | 8/1980 | Allen et al. ........................... 43/125 |
| 4,270,658 | 6/1981 | Schuster ............................. 206/439 |
| 4,487,791 | 12/1984 | Komatsu et al. ..................... 428/138 |
| 4,597,218 | 7/1986 | Friemel et al. ........................ 43/131 |
| 4,657,804 | 4/1987 | Mays et al. .......................... 428/212 |

Primary Examiner—Marion C. McCamish
Attorney, Agent, or Firm—Millen, White & Zelano

[57] ABSTRACT

A fumigant applicator for releasing therefrom a volatile substance, e.g., phosphine from a metal phosphide, at a controlled rate, thereby avoiding excessive local phosphine build-up and with complete protection of the contents against liquid water, in the shape of a sachet at least one face of which is formed from a spun-bonded, polyolefin sheet or fleece of heat and pressure bonded polyolefin fibers, which is vapor- and gas-pervious but impervious to liquid water and use, naturally water-resistant and of high tensile and tear strength, which sheet or fleece is rendered heat-weldable and is heat-sealed at its edges by a high porous coating, preferably a powder sprinkle coating, of a thermoplastic heat welding bonding layer which melts lower than the polyolefin fibers so that a heat welding seam at the edges of the sheet can form before the fibers melt so that the physical properties of the polyolefin fibers and the gas permeability thereof are substantially unaffected.

36 Claims, 4 Drawing Sheets

FUMIGANT APPLICATOR

BACKGROUND OF THE INVENTION AND PRIOR ART

The present invention relates to a novel, fumigant applicator formed from a heat weldable plastic sheet material comprising a spun-bonded, preferably paper-like, polyolefin sheet or fleece composed of heat and pressure bonded minute polyolefin fiber which is vapor- and gas-pervious but impervious to liquid water and dust, naturally water-resistant and of high tensile and tear strength. More particularly, this invention relates to a fumigant applicator formed from this sheet material which contains a gas- or vapor-evolving pest control agent, more particularly comprising a hydrolyzable metal phosphide from which, when exposed to environmental humidity, phosphine gas is released to the environment due to the hydrolysis of the metal phosphide.

A sheet or film material as described above is known. Certain embodiments thereof are marketed under the registered trade mark TYVEK of Du Pont de Nemours. This family of tough, durable products is made from 100% high density polyethylene fibers by an integrated spinning and bonding process. The sheet is formed by spinning very fine polyethylene fibers, which in practice, i.e. in the commercial product, are approximately 0.005 mm in diameter and laying these down as a random network, the fibers then being bonded together with heat and pressure. No binders, sizes or fillers are used in that commercial product. The product is available in various degrees of stiffness or softness and drapeability, most of them being paper-like, i.e., having the appearance of ordinary wood pulp paper, and in various degrees of porosity. The toughness and puncture resistance thereof is outstanding compared to other materials. The combination of tensile strength, elongation, tear strength and flex-life is considered unique. The surface can be made smooth and compact, suitable for printing, coating or laminating. The product is naturally water-resistant, meaning that its physical properties are unaffected when immersed in water. The product has excellent dimensional stability, rot- and mildew-resistance and chemical resistance. Melting occurs at 135° C. Compared with many other plasticsbased materials, this product has favorable nonflammability properties. The product shrinks away from flame but will burn slowly and drip melted polymer. The product does not generally shed lint particles under conditions of ordinary use. Most such products are marketed with effective antistatic treatment. Most of the products, and in particular those of paper-like consistency have good liquid hold-out characteristics, i.e., supporting hydrostatic heads of aqueous liquid up to and exceeding 76 cm. These products have been recommended for example for the manufacture of tags and labels, banners and signs, wall covering, book covering, wall maps, charts, packaging and post envelopes.

The above listed properties are highly desirable. However, the present applicants intended to put these properties to commercial use in a particular new manner of application where certain problems were encountered.

The applicants recently developed (see U.S. Pat. No. 4,597,218; Eu-PS 0131 759) what is presently considered to be a new generation of applicator means for holding a gas evolving pest control agent, more particularly comprising a hydrolyzable metal phosphide, from which, when exposed to environmental humidity, phosphine gas is released to the environment due to the hydrolysis of the metal phosphide. Such applicator means are an the form of sachets, i.e. relatively small bags or envelope-like pockets, made of a non-woven thermoplastic sheet material (by some authors now-a-days referred to as "fleece") comprising more or less randomly orientated fibers of a thermoplastic polymer which are bonded together, usually with heat and pressure to form a felt-like or matted texture. These are usable as individual sachets or in the form of a plurality thereof joined together in a flat composite structure, e.g. flexibly, such as an elongate belt adapted to be rolled up in a or folded up concertina-like manner for storage and transport, packed in airtight and moisture-proof containers such as sealed tins. These applicators are removed from the airtight container immediately prior to use and are then unrolled or unfolded (in the case of such belts) and exposed to the environment where fumigation is to take place (PCT Application WO-A-80/00119). The residue of the hydrolyzed metal phosphide is retained in dust form by the applicator. These applicators are manufactured by thermal welding, the resulting welding seams serving to close the sides of the sachets or the like and to form flexible hinge lines between individual sachets. The flexibility of the seams and their physical strength is of obvious importance in the case of the aforesaid belt-like composite applicators, and is even important in the event that individual sachets are to be manufactured, because the manufacture thereof takes place in substantially the same manner as that of the composite belts (known in the art as "bag blankets") until the final manufacturing stage, when the continuous belts delivered by the machine and filled with pest control agent, are cut along the seam lines into individual sachets.

The teachings of U.S. Pat. No. 4,597,218 introduced substantial improvements into the art. However, the tear-resistance of all those non-woven fabrics ("fleeces"), which could be heat-welded satisfactorily, proved to be somewhat limited. Under severe conditions of use or abuse, these applicators might still tear and burst open. Also, the best materials tested were nevertheless often found to be not entirely dust-proof in the sense that when a sachet filled with very fine dust is beaten against a very clean, polished surface, traces of dust penetration can be observed. These properties can be objectionable if extreme hygienic demands must be met. None of the many prior art non-woven weldable fabrics tested had the property of forming (for practical purposes) a complete barrier against liquid water and yet were pervious to a desired extent to water vapor and the phosphine gas released by the metal phosphide.

Finally, in spite of the many desirable properties of the aforesaid "new generation" applicators, they still suffered from the defect that the non-woven material itself exercised little or no control over the rate of access of water vapor to the pest control agent and over the rate at which the vaporous or gaseous contents of the applicators were released to the environment. One result has been an accumulation of sometimes extremely high concentrations of phosphine gas in the immediate vicinity of the outer surfaces of the applicators, whereas it would have been desirable for these gases to be released more gradually and at a rate closer to that at which the gas is distributed in the environment to be fumigated by diffusion, circulation, convection or other mechanisms. Excessive local accumulations of phosphine occur particularly during the first few hours of exposure to the environment and particularly at high ambient temperatures. These local accumulations are not only undesirable for well known safety reasons, but also for pest control purposes. Excessive sudden phosphine concentrations can put insects into a comatose state in which they cease to inhale the gas and from which some insects may subsequently recover. A gradual, even release and distribution of the gas is therefore desired. But in previous uses and tests the plastics fleeces previously employed did not achieve or contribute to this desired effect.

The applicants tested and investigated the film material set out further above and found its properties ideal in many respects for the purposes of the just described applicator means. Inter alia the tear strength and dust-proofness were found to be greatly improved as compared with previously tested materials. However, it was found impossible to heat-weld the material in the required manner and particularly not with the means available for the manufacture of the prior art sachets. If sufficient heat and pressure was applied to achieve a satisfactory bond, the properties of the fibers were destroyed. The welding seams became transparent and brittle and the sachets were liable to burst open and release the poisonous composition or the dust-like decomposition products of the metal phosphide.

Several attempts were made to solve the problem by first having the sheet material coated on one side with a bonding layer, e.g. of ethylene vinyl acetate (EVA) having a melting point or region lower than that of the sheet material. Successive samples produced by various coating or laminating processes did not meet the requirements, because in those cases where heat welding could be applied successfully, the required permeability to water vapor and released phosphine gas had been lost.

OBJECTS OF THE INVENTION

It thus became necessary to find a solution to this problem and to develop a new sheet material as set out in the introduction, which combines the desired properties of the prior art sheet material with a desired heat weldability suitable for producing welding seams with available equipment and wherein desirable properties of the sheet material, in particular the high tear strength are retained. The judicious and skilful applications of the teachings which follow provides such a solution. Moreover, by an appropriate selection of the sheet material, it is now possible to produce applicator means for pest control agents of the type discussed above which have desirable properties unequalled by the prior art applicators. In particular it was found quite unexpectedly that the new applicator means which the present invention provides, makes possible a hitherto unattainable control of the rate of release of gas and that this property can be employed to avoid undesired levels of localised gas accumulation to an extent considered unattainable previously.

Further and alternative objects and advantages of the invention will become apparent from what follows.

SUMMARY OF THE INVENTION

In accordance with one aspect of the invention, there is provided a heat weldable plastic material as described above which is coated at least in areas and on a side so as to render if heat weldable with a thermoplastic highly porous heat welding bonding layer having a melting point or region sufficiently lower than that of the polyolefin fibers that conventional welding with heat and pressure results in a welding seam before the fibers reach their melting point so that the physical properties of the polyolefin fibers are substantially retained.

The difference in melting points or melting regions between the polyolefin fibers and the bonding layer should be more than 20° C., e.g., between 30° and 80° C., more preferably between 40° and 70° C., and in the preferred embodiment, from about 50° to 60° C. lower.

The permeability to gas and moisture of the bonding layer should be of an order of magnitude substantially higher than that of the polyolefin sheet, particularly if such layer covers the entire surface of the polyolefin sheet. The latter is preferred for reasons of simplicity of manufacture of the sheet material and also of use of the sheet material, because in that event welding need not be confined to predetermined coated areas of the sheet material. On the other hand, it will be appreciated that savings in respect of the material forming the heat welding bonding layer can be achieved if such layer is confined to predetermined regions where the welding seams are to be formed. If the permeability exceeds by orders of magnitude the permeability of the polyolefin sheet, the latter will determine predominantly the permeability of the sheet material as a whole and the bonding layer will have no great effect.

The permeability of the bonding layer depends on two factors:

(a) the thickness of the layer expressed in amount of bonding material per unit of surface area and (b) the manner of application of the heat welding bonding layer, the latter factor being of particular importance.

The applicant attempted to attain the objects of the invention in a variety of ways without success. For example (e.g. in the case of EVA being selected as the bonding material) attempts were made to achieve the desired object by laminating a foil of EVA (albeit thin) onto the sheet material. However, the required vapor perviousness was lost.

On the other hand, it has been found that the bonding layer can be formed successfully by methods comprising sprinkling the bonding substance in powder form onto a supporting surface and fusing the substance onto that surface so that a high porosity is retained.

For example, the powder can be sprinkle-coated directly onto the polyolefin sheet followed by fusing at a temperature below the melting point or melting region of the fiber of the sheet. This is possible with accurate temperature control in spite of the relatively small difference in melting points between the polyolefin fibres and the bonding substance, e.g. by passing the sheet with the sprinkled-on powder through a heating tunnel of adequate length and carefully controlled temperature.

A preferred method comprises what is known in the art as reverse coating, i.e. a method in which the bonding powder is first sprinkle-coated onto a temporary support onto which it is fused to form a porous fused layer, this porous layer then being transferred and bonded onto the polyolefin sheet, which thereby substantially retains its porosity.

Suitable amounts of coating material for forming the bonding layer were found to be in the range of from about 10 to about 50 g/m$^2$, more particularly 15 to 40

$g/m^2$ and preferably 15 to 30 $g/m^2$. 30 $g/m^2$ were found to give very satisfactory results when using EVA as the bonding material. However, even 20 $g/m^2$ was found to be quite sufficient.

The material for the bonding layer is chosen to be compatible with the polyolefin sheet and also with a view to rendering the sheet material heat-weldable, firstly with itself, but preferably also with other foils or films, e.g. of non-woven fabrics, e.g. made of polyolefin, i.e. polyethylene, polypropylene and copolymers thereof, polyesters or mixtures of two or more of the aforegoing. This requirement is met very satisfactorily by EVA which is the preferred bonding material, a preferred grade having a melting region of about 75° to 80° C. where the fibers of the polyolefin sheet which have a melting point of about 135° C.

Although less preferred, it is also possible to employ a polyolefin bonding layer, e.g. polyethylene, either high density or low density and preferably in the same melting point range as set out above, i.e. preferably 80° to 85° C., if the melting point of the fibers is 135° C. Tests have shown that polyamides or polyesters and suitable blends of the exemplified substances having the required melting point or region can also be used, but are at present not preferred.

The polyolefin of the polyolefin sheet is preferably polyethylene and in particular high density polyethylene, e.g. having a melting point in the region of 135° C. However, in principle other polyolefins may be employed, e.g. polypropylene, mixtures or blends of high density polyethylene and polypropylene or polyethylene polypropylene copolymers.

It must be stressed that the spun-bonded polyolefin sheet material employed in accordance with the present invention has characteristics and properties vastly different from the spun-bonded polyester used in connection with so-called "Ropes" as described in U.S. Pat. No. 4,653,644. The spun-bonded polyester there described neither has the strength nor the impermeability to liquid water and to dust which constitute such important characteristics of the polyolefin material used in accordance with the present invention for most of the purposes described in the present application. The spun-bonded polyester sheets also do not have the desirable property of limited gas and vapor permeability which, according to the present invention can be used to control the rate at which gases or vapors are emitted from applicator means in accordance with the invention which are to be described further below.

If it is desired to apply the bonding layer to restricted portions of the sheet material, that is to those regions which are to be welded, this may be achieved by any of the methods described in U.S. Pat. No. 4,597,218.

The sheet material in accordance with the invention can be put to a number of uses in trade and industry, subject to an appropriate choice of sheet material for the particular purpose (e.g. in respect of density, flexibility, porosity and surface finish). For example, it can be used for producing a variety of products (known per se in other respects) by heat welding, employing relatively simple equipment, without damaging the fiber properties or other desired characteristics of the film. The polyolefin sheets suitable for the invention include sheets of such fine porosity that they are impervious even to bacteria. Sheet material according to the invention produced from such sheets can accordingly be employed for the sterile packaging, e.g. of medical, surgical, dental or sanitary products and instruments by thermal welding.

Other potential uses are sachets for drying agents, e.g. silica gel and postal envelopes.

However, according to a preferred and important aspect of the present invention, there is provided an applicator for holding a gas evolving pest control agent described above, wherein the sachets or pockets are formed by thermal welding from sheet material comprising at least one layer or portion of a layer of sheet material in accordance with the invention as defined above.

More particularly, each sachet or pocket is formed of two sheets of sheet material, heat welded alongside thereof, to form welding seams, at least one of which sheets, and preferably both is/are a sheet material according to the present invention.

The invention according to a further aspect provides an applicator means for holding a gas-evolving or vaporevolving pest control agent or substance comprising at least two sheets of sheet material bonded together by heat-welded welding seams to form a pocket or pockets for containing a substance from which vapors or gases are to be released, one sheet being composed of a spunbonded, preferably paper-like, polyolefin sheet or fleece composed of heat and pressure bonded minute polyolefin fibers which is vapour- and gas-pervious but impervious to liquid water and dust, naturally water-resistant and of high tensile and tear strength, and another sheet being composed of a suitable thermoplastic foil or film weldable to the former and having a melting point or region sufficiently lower than that of the spunbonded polyolefin sheet to permit heat welding of the former to the latter substantially without damage to the latter and without a special bonding layer.

These aspects of the invention are based on more than one inventive step. Inventiveness resides in the weldable sheet material according to the invention from which the applicator means is made, but also in the selection of the polyolefin sheet used for manufacturing the weldable sheet material. In the light of years of experimentation with a large number of gas-pervious synthetic resin sheet materials including fleeces, it came as a great surprise that this particular type of sheet material would afford protection to metal phosphides and be capable of regulating the rate of phosphine release in the manner and to the extent herein disclosed, something which in the light of previous experience was considered unattainable by those skilled in the art. For purposes of the applicator means this polyolefin sheet affords the unique property of its remarkable imperviousness to liquid water. Accordingly, the present invention for the first time permits the manufacture of pest control sachets and like applicators containing a metal phosphide protected completely against liquid water under conditions of normal use and abnormal conditions which may occur accidentally in such use, entirely due to the water barrier effect of the polyolefin sheet. From a safety point of view this is of major importance, because without such protective effect metal phosphide compositions may autoignite spontaneously on accidental contact with liquid water. This may happen for example due to dampness or wetness of grain or other agricultural produce to be fumigated, ingress of rain due to inadequate coverage or leaking storage facilities and such like. In the context of selection, the printability and the antistatic properties of the sheet material are also important properties, particularly the latter which decreases potential explosion hazards and assists in certain forms of printing. The readily attainable great smoothness of the sheet material is a further advantage in practice. Yet another advantage is the fact that the sheet material as such has very low flammability. It can hardly be induced to burn and once this has happened, it will burn very slowly.

After the extensive and initially unsuccessful experiments conducted with the commercially available polyolefin sheet or fleece, it also came as a surprise when eventually a solution was found to the problem of coating the material to render it heat-weldable without adverse effect on the remaining desired properties. The applicator means according to the various above-defined aspects thereof, if the present teachings are followed, are capable of attaining the common object of providing unique protection against liquid water to pest control agents, in particular those based on metal phosphides, even in the absence of protective ingredients conventionally employed and of retaining the agent and the residues of the spent agent, even when in the form of very fine dust, in a more reliable manner than previously achieved. Moreover, these applicators attain the novel object of being adaptable to regulating in a predeterminable manner the rate at which volatile contents or products of such contents (e.g. $PH_3$) are released to an environment.

Perhaps most important of all, it was found surprisingly that the local concentrations of phosphine gas at or near the surface of the applicator means were very much lower under practical conditions of use, than in the case of the best prior art devices previously available. In this respect the new applicators proved superior by a whole order of magnitude. This improvement was neither expected nor predictable.

The scope of the invention extends to the applicator means as set out above in which the sachets or pockets contain a metal phosphide pest control agent, e.g. based on aluminium phosphide, magnesium phosphide, calcium phosphide or more than one of these, aluminium phosphide and magnesium phosphide being preferred.

Moreover, for the first time it is now possible to employ any of these metal phosphides in the applicator means without any additives at all and in particular without the additives which are conventionally used to protect against liquid water. It is quite remarkable that this has now become possible even with technical magnesium phosphide, a substance which is so highly reactive that it can normally be protected only with great difficulty against autoignition on contact with liquid water, even when contained in some commercially available applicator devices.

The invention thus extends to embodiments wherein the agent is based on aluminium phosphide, magnesium phosphide, calcium phosphide or more than one of these.

The polyolefin sheet is selected according to the gas and vapor permeability required to attain a desired gas generation rate. It is thus possible to control the rate of phosphine generation purely as a function of the permeability of the sheet material. Moreover, it is possible to do so to a substantial degree regardless of the ambient relative humidity in the fumigation environment. The choice of porosity thus becomes a more dominantly controlling factor even than temperature, because the permeability which controls the rate at which humidity can enter the applicator from the environment is not as highly temperature dependent as it is dependent on the porosity.

It is thus possible to produce applicators designed to release phoshine gas at different predetermined rates, depending on requirements, because in some cases it is desired for phosphine gas to be available relatively quickly, whereas in other cases it is desirable for the release to be relatively slow.

Purely by way of example, the moisture permeability (expressed as $g/m^2/24$ h) may for example vary from about 50 to 2000, to cover on the one hand applicators designed for very slow release and on the other hand those which are designed for relatively fast release.

Permeabilities from about 300 to 1000 would be more suitable for average situations, and for the most commonly desired fumigation purposes one would select a material with a moisture permeability of from 500 to about 750, say about 600 to 630. Typical such polyolefin film material (i.e. before the application of the bonding layer) will have a nominal weight (expressed in $g/m^2$) between 30 and 150, more generally from about 50 to about 120 and typically about 60 to 90, say 75.

An alternative for restricting the rate of gas release in a controlled manner, will be by restricting the available gas-pervious surface area of the sheet material per unit of composition enclosed in the applicator means. This may be achieved, e.g., by (a) Making the applicator means partly (e.g., on one side) of sheet material according to the invention and for the remainder of a different but compatible sheet material having little or no gas and vapor permeability, e.g. a dense thermoplastic foil;

(b) Coating a predetermined proportion of the gas-pervious surface area with a coating of little or no permeability.

The rate of gas release will be inversely proportional to the surface area which is pervious to gas and moisture.

In the case of (a), if the impervious foil has a melting point or region sufficiently lower than that of the fibers of the spunbonded polyolefin, it will even be possible to heat-weld the two materials together without the need for a special bonding layer. The impervious foil will then itself act as the bonding layer. Such applicator means may then be defined as comprising at least two layers of sheet material bonded together by heat-welded welding seams to form a pocket or pockets for containing a substance from which vapors or gases are to be released, one layer being composed of the type of spunbonded polyolefin sheet as defined and described in the context of the heat weldable plastics sheet material, and another layer being composed of a suitable thermo-plastic foil or film weldable to the former and having a melting point or region sufficiently lower than that of the spunbonded polyolefin sheet to permit heat welding of the former to the latter substantially without damage to the latter. As for the remainder the teachings herein relating to the applicator means may be applied in an analogous manner.

The contents of the applicator means need not be in powder form. They can also take the form of granulates or pressed bodies, e.g. pellets or tablets. In the latter case the applicator means may be used as a superior modification of devices which have become known in the art as "Ropes", as described in U.S. Pat. No. 4653,644, where pellets of nearly spherical configuration are enclosed individually in small cup-like pockets of a non-woven fiber sheet (fleece). In practical tests these ropes suffered from the disadvantage that they released dust. If the heat weldable sheet material according to the invention is used a much superior product results.

The scope of the invention also extends to a method of disinfesting commodities, buildings, packaging means, transport means, e.g. vehicles or shipholds or transport containers by releasing phosphine gas there into from applicator means as described above and maintaining a pesticidal concentration of phosphine gas for a period effective to achieve disinfestation. This aspect of the invention can also be described as a method of protecting such commodities and the like as listed above against deterioration or for improving the quality or usability thereof.

In accordance with a modification of the invention the afore-described applicator means may also be employed for enclosing and releasing to the environment other suitable pest control agents, e.g. those which do not rely on hydrolysis but which release pesticidal vapors due to their inherant vapor pressure under the conditions of use. Examples are paradichlorobenzene (used for combatting textile moths), Dursban or Dichlorvos absorbed in a suitable carrier medium or napthalene. Details require no description.

In accordance with yet another modification the applicator may be employed in an analogous manner for the slow-release of other volatile substances contained in the applicator means, e.g. air freshener substances, scents, or insect or animal repellants.

In the following the invention will be further explained by way of specific examples, but it should be noted that the invention is not limited to the examples given and that the specific examples should be read together with the more general preceding disclosure which will enable the person skilled in the art to practice the invention within the full scope of the claims.

DETAILED DESCRIPTION OF SPECIFIC EMBODIMENTS

Although the invention should be readily understandable to those skilled in the art from the aforegoing detailed description, those features lending themselves to pictorial representation will be briefly described in the following with reference to the drawings which are not to scale. The description which now follows should be read in conjunction with the details of the aforegoing description.

Figure 1:
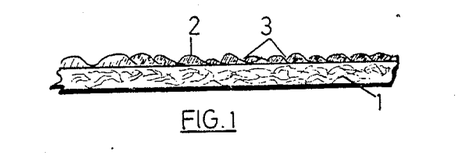
FIG. 1 represents a diagrammatic cross-sectional view of a portion of a weldable sheet material in accordance with the invention.

Referring now first to FIG. 1, there is shown in section a sheet 1 of vapor permeable, substantially anhydrous non-woven fabric, being a spun-bonded paper-like polyolefin sheet composed of heat- and pressure-bonded minute polyolefin fibers, which while being vapor- and gas-pervious, is impervious to liquid water and dust, is naturally water-resistant and of high tensile and tear strength. For purposes of the present example it is assumed that this sheet material is a product as manufactured and marketed by or on behalf of Du Pont de Nemours under its trade mark TYVEK, code numbered Type 1073D.

The material has a mass of about 75 g/m², a thickness of about 200 microns, a nominal moisture permeability MVT of 614 g/m²/24 h. Its tear resistance according to Elmendorf is 545/500 (ASTM D 689-62) gMD/XD. Its tensile strength (ASTM D 828-60) is 7,5/8,8 kg/cm MD/XD. Its elongation to break (DIN 53857) is 26/32% MD/XD. It has an air permeability of 23 sec (Gurley Hill). Unpressurized liquid water will not penetrate through the sheet material. It has a smooth surface finish. The melting point of the fibers which have an individual thickness of 0,005 mm is about 135° C.

The sheet material 1 carries a porous coating 2 having a rough surface finish composed of EVA of melting point 75° to 80° C., applied at an average rate of about 30 g/m² by so-called reverse coating, i.e. a method in which EVA powder is first sprinkle-coated onto a temporary support onto which it is fused to form a porous fused layer which is then transferred and bonded while still in a fused state onto the polyolefin sheet, while substantially retaining its porosity. The drawing shows diagrammatically the rough finish of this coating and that the powder particles have been fused only to the extent that they have not been fused together completely, forming individual gooseflesh-like humps with substantially open pore areas 3 therebetween. The EVA coating is present on one side of the sheet only and its porosity is so high that it virtually does not interfere with the gas and vapor permeability of the sheet.

Figures 2, 3, 4, 5:
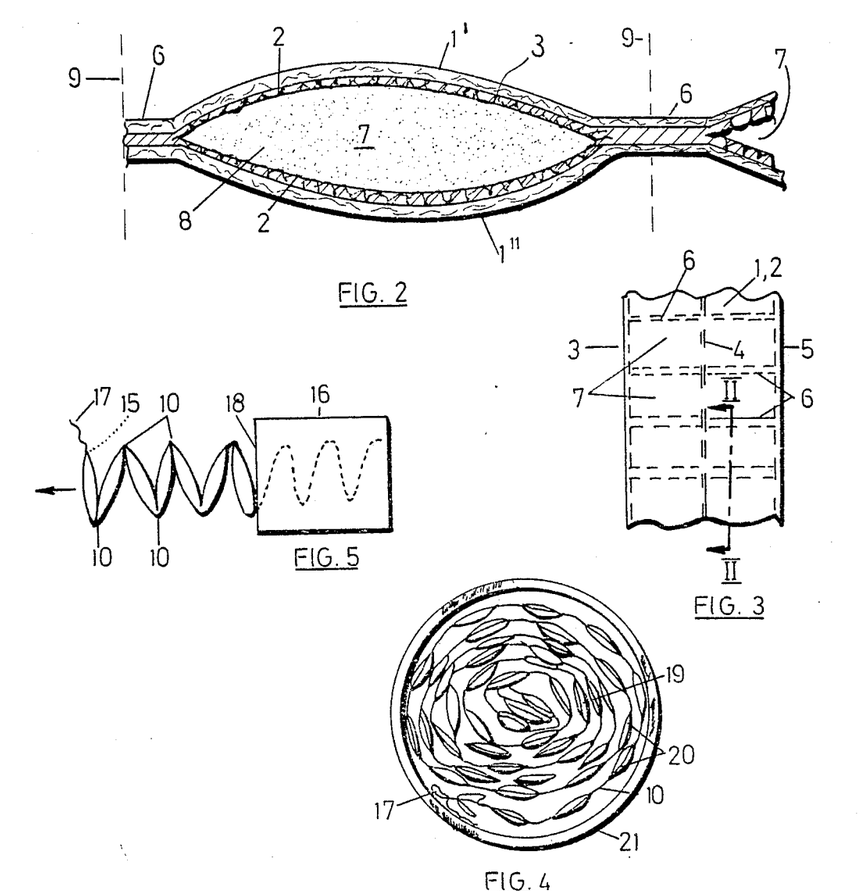
FIG. 2 represents a section through a fumigant applicator means according to the invention made from a sheet material as shown in FIG. 1.
FIG. 3 represents a plan view on a smaller scale of the applicator means, part of which is shown in section along line II-II in FIG. 2.
FIG. 4 represents a top view on a tin can (lid removed) containing an alternative embodiment of a multiple sachet device according to the present invention for use as a fumigant applicator.
FIG. 5 represents on a smaller scale a diagrammatic side elevation of one embodiment of a multiple sachet belt according to the invention in the process of being withdrawn from its package.

Referring now to FIG. 2, a multiple sachet is shown in section composed of two sheets 1' and 1" corresponding to sheet 1 in FIG. 1, each coated on one side with EVA 2, the coated side of the two sheets facing each other.

As shown more specifically also in FIG. 3 in plan view, the two layers of sheet material 1,2 have been heat-welded along longitudinal welding seam lines 3, 4 and 5 and along transverse heat-welded seam lines 6 to form two parallel longitudinal rows of sachet-like pockets 7, each pocket containing a measured amount of aluminium phosphide or magnesium phosphide powder with or without additives. The welding seam lines 3 and 5 form the two sides of the belt-like device, while the longitudinal seam 4 is centrally longitudinally disposed. The welding seam lines are produced by heat-welding means as employed in machines for the continuous packaging of commodities in thermoplastic films. Such heat welding with pressure at a temperature sufficiently high to cause fusion of the EVA, but not high enough to cause any fusion of the fibers of the sheets 1 (1', 1'') causes complete bonding together of the two sheets along the welding seam lines as shown in FIG. 2.

As regards the contents 8 of pest control agent inside each cavity 7, reference is made to the teachings of U.S. Pat. Nos. 4,597,218 and 4,215,508 and PCT Application WO-A-80/00119 (corresponding to ZA-PS 79/2263) and corresponding patents in many other countries. However, it should be noted that for the reasons stated above, it is now possible to omit the additives of the metal phosphide compositions entirely and to use instead an additive-free or substantially additive-free metal phosphide powder or granulate, more particularly technical magnesium phosphide or aluminium phosphide (the meaning of which terms is well known in the pest control art). Nevertheless, it is preferred to impregnate the metal phosphide with a minimum amount of hydrophobizing agent in a manner known per se, e.g. 1 to 5, say 3% solid paraffin, or an organo silicon compound, more particularly as disclosed in U.S. Pat. Nos. 4,421,742 and 4,600,589, particularly because this also affords protection during manufacturing stages preceding the sealing of the products into the applicator. The amount of metal phosphide is so chosen that for each pocket or sachet between 5 and 15 g available (i.e. releasable) phosphine are provided, 11.32 g available phosphine being the standard for aluminium phosphide compositions in sachets.

Optionally, the individual sachets may be cut apart along cutting lines 9 which pass through the center of each welding seam separating the individual cavities 7 from one another. In this form individual sachets are formed which may be packed individually or in predetermined numbers in air-tight containers for storage and transport. In this manner access of moisture to the metal phoshide is prevented until the package is opened and the sachets are removed for use as fumigation applicators.

However, as shown in FIGS. 3, 4 and 5, the applicator means according to the invention may also be present in the form of belts of predetermined length comprising in the shown example two parallel rows of interconnected sachets, e.g. altogether 100 sachets which in a rolled-up or folded condition are stored in air-tight containers until used.

Referring to FIG. 5, a multiple sachet as described with reference to FIGS. 2 and 3 is shown in side elevation. The areas 10 represent the transverse welding seams 6 which separate the individual sachet pockets filled with pest control agent. The last such welding seam, being a strong and relatively tear-resistant region, has been provided with an aperture 15 for the attachment of the applicator means, e.g. by means of a string passed through the hole 15. Optionally the hole 15 may be reinforced with a metal or plastics eyelet. The multiple sachet belt device is packed folded in concertina fashion in a gas-tight container 16. The concertina folds coincide with the transverse welding seams 10 between the individual sachet pockets. In FIG. 5 the container 16 has been opened on one side 18, through which the device is shown being withdrawn in the direction of the arrow.

Referring now to FIG. 4, an alternative embodiment of a multiple sachet belt device 19 is shown composed of a large number, e.g. 100 individual sachets 20, interconnected via welding seams 10 (corresponding to welding seams 6 in FIGS. 2 and 3) to form a continuous belt-like device rolled up and accommodated inside the gas-tight tin can 21. Again, one end of the device is fitted with a fastening string as in FIG. 5.

In tests the new applicator means proved to be so strong and completely dustproof as to eliminate for all practical purposes any risk of even minor amounts of poisonous dust entering the environment, e.g. foodstuffs or feeds treated with the fumigant. For that reason the applicator means according to the invention (sachets or belts) can now be contacted directly with sensitive food products, e.g. flour, rolled oats, infant food, dried fruit, nuts and tobacco, without the prior art need to interpose paper bags, cartons or similar partitioning means. Sachets left in the commodities by accident are quite unlikely to be ripped open when the commodities are moved, e.g. for re-storage or transport, as happened occasionally with prior art paper sachets.

Figure 6:
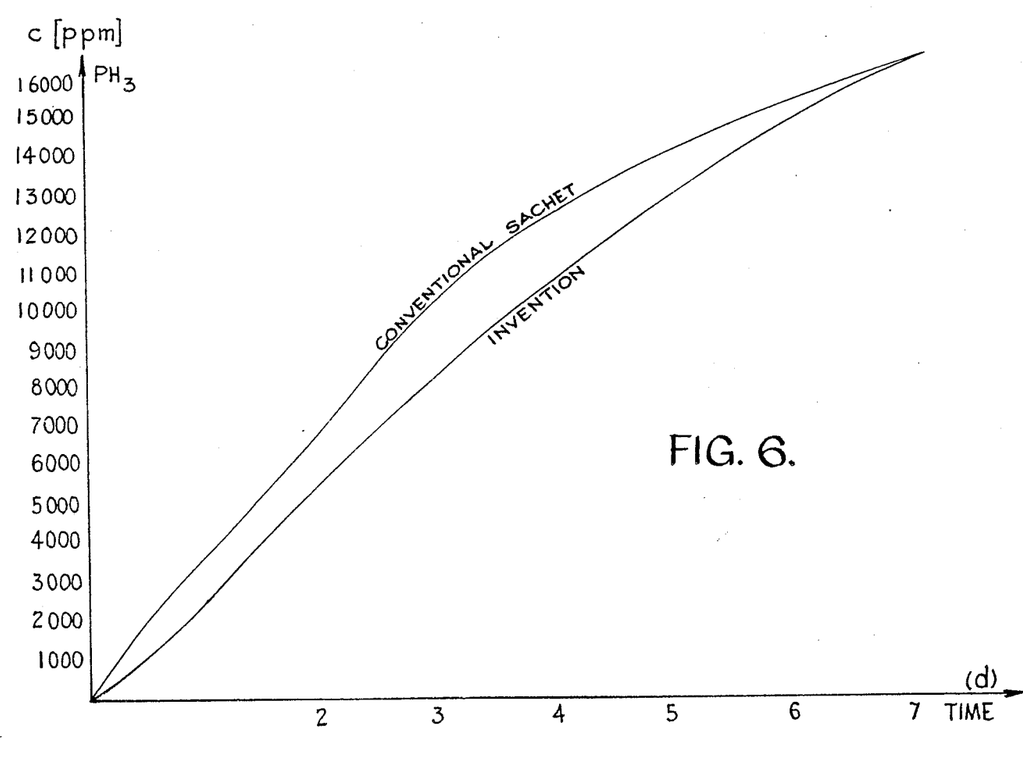
FIG. 6 represents gas release curves obtained with a conventional paper sachet and a sachet according to the invention, each containing technical aluminium phosphide with 11.32 g available $PH_3$.

The gas generation characteristics of a sachet according to the invention (FIG. 3) are compared with those of a conventional paper sachet in FIG. 6. The conventional technical aluminium phosphide used was not treated in any way which might have affected the gas generation characteristics. It was employed as a conventional mixture of 70% w/w of technical aluminium phosphide powder and 30% inert ingredients. The sachets were tested in a gas-tight test chamber (0,5 m$^3$) at 70% relative humidity and 20° C.

It will be seen that the gas generation from the sachet according to the invention was very even, following an almost rectilinear pattern up to day 7, when the contents of available $PH_3$ had been exhausted.

Figure 7:
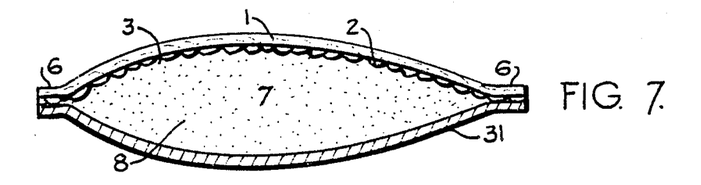
FIGS. 7 to 11 represent sections similar to FIG. 2 of various alternative embodiments of fumigant applicators according to the invention which in the case of FIGS. 7, 8 and 10 are made partly of sheet material as shown in FIG. 1. All of these are illustrated as individual sachets but they could also be in the form of a plurality of sachets, i.e. a multiple sachet device as described more fully with reference to FIGS. 2, 3, 4 and 5.
Figure 8:
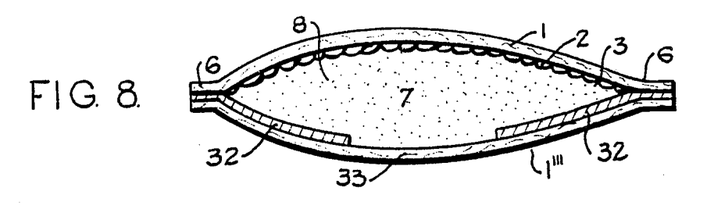

Referring now to FIGS. 7 and 8 of the drawings, one side of each of these sachets is again in each case formed by a sheet as described with reference to FIG. 1, the reference numbers having the same meanings as there described, whereas the opposite side of the sachet is formed of a different sheet material. The two sheets being heat-welded together at 6 along the edges of the sachet. In FIG. 7 this different sheet material 31 is a substantially gas-impervious material and could for example be either a polyolefin-aluminium foil laminate or a substantially gas-tight multiple laminate of polyethylene and a substantially more gas-tight synthetic resin, for example polyvinilidine chloride (PVDC). Accordingly, the sachet in accordance with FIG. 7 will admit humidity to the interior 7 containing the metal phosphide composition in powder or granulate form (indicated diagrammatically by a multitude of dots 8) at approximately half the rate at which such humidity would be admitted if both sides were composed of the same sheet 1, 2, 3. Accordingly, in this case the phosphine gas is generated and released similarly at half the rate at which this occurs in the case of sachets as illustrated in FIG. 2.

Referring more specifically to FIG. 8, the second sheet 1''' is again composed of the same spun-bonded paper-like polyolefin sheet as in the case of the first layer 1, but without the sprinkle-coated porous layer 3. Instead thereof portions 32 of the sheet 1''' are coated with a dense coating of fused EVA powder which for practical purposes prevents access of humidity to those portions. This means that the access of humidity is restricted to the surface area of the sheet 1 on one side and to the uncoated portion 33 of the second sheet 1''' resulting in a phosphine gas generation rate proportional to the rate of humidity admission.

Figure 9:
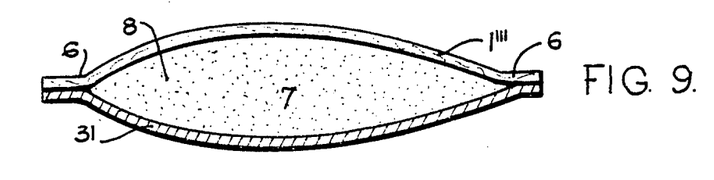

Referring now to FIG. 9, one side of the sachet there shown is composed of a sheet 1''' as in FIG. 8, devoid of a sprinkle-coated porous layer 2, 3, whereas the other side is formed of a dense substantially gas and moisture-impervious sheet material 31 which is heat-welded along seams 6 as in FIGS. 7 and 8 to the sheet 1''' to form the sachet cavity 7 filled with pest control agent 8. At least that side of sheet material 31 which faces the sheet 1''' has a melting region lower than that of the fibers of sheet material 1''', sufficiently so to permit heat welding without fusing the polyolefin fibers of sheet 1'''. Alternatively, a suitable melting adhesive layer may be applied in the position of the welding seams 6 prior to heat welding, for example in the manner shown in FIG. 11 to be described further below. The rate at which humidity will be admitted to the pest control agent 8 and phosphine gas will be generated, will be substantially similar to that of a sachet as described with reference to FIG. 7.

Figure 10:
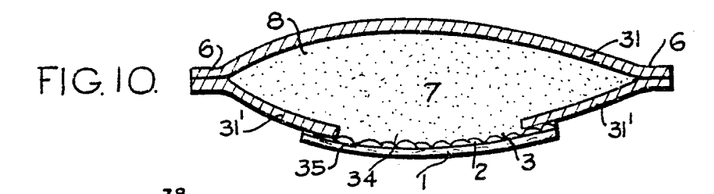

Referring now to FIG. 10, yet a further modification is shown of the embodiment of a sachet described with reference to FIGS. 7, 8 and 9. In this case one side 31 of the sachet is again composed of substantially gas and humidity impervious sheet material 31. The second side is composed in part of strips 31' of the same gas and humidity impervious sheet material, leaving therebetween a gap 34 which is covered by a gas and humidity pervious strip 35, of the sheet material 1, 2, 3 described with reference to FIG. 1. This strip 35 is heat-welded onto the edges of strips 31' in the regions of overlap. The edges of the sachet are heat welded at 6 as in all previous embodiments. If the strips 31' are by themselves heat-weldable to strip 35, without the need of the bonding material 2, the bonding layer 2, 3 may be omitted. Alternatively, the bonding material may be confined to the regions of overlap. In this embodiment the admission of humidity is substantially confined to the region 34 and controlled by the permeability of the material 1, 2, 3 in that region. The size of region 34 therefore controls the rate at which the pest control agent 8 generates phosphine gas and releases it to an environment to be fumigated. The embodiment according to FIG. 10 can be modified in a variety of manners. The strip 35 need not be symmetrically disposed as shown, but instead there may be a single strip 31', and a single strip 35 which at the same time replaces the second strip 31''. Also, instead of strips 31' being heat welded to sheet 31 along the seams 6, the strips 31' may be formed by folding over the edges of strip 31.

Figure 11:
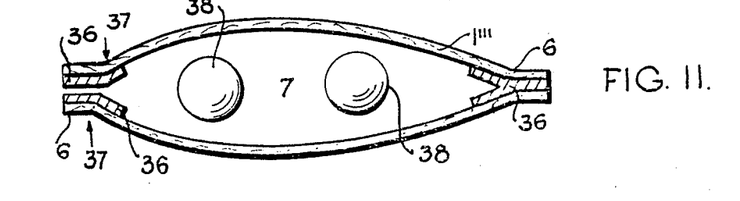

Referring now to FIG. 11, an alternative embodiment of an applicator device according to the invention is shown in which both sides of the sachet are composed of uncoated spun-bonded polyolefin sheet 1''' as used for example in FIG. 9. However, in this case the welding regions, where the edge seams 6 are to be formed have been coated with bonding layers 36 of e.g., EVA having a melting point substantially lower than that of the fibres of layer 1'''. On the right hand side of FIG. 11 the bonding layers 36 have already been fused together at 6, whereas on the left hand side the two bonding layers are about to be pressed and heat welded together as indicated by arrows 37.

In this embodiment as in all previous embodiments, the cavity 7 may be filled with a metal phosphide composition, e.g. in powder or granulate form. However, this embodiment as well as all previously described embodiments can also be used for alternative purposes. In the case illustrated the cavity 7 contains conventional mothballs 38, e.g., of naphthalene. The sachet serves to prevent direct contact of the naphthalene with e.g., articles of clothing to be protected against moths. The sachet also controls the rate at which the naphthalene is released to the environment. In this as well as in all previously described embodiment of sachets, the mothballs 38 may also be replaced by different bodies containing a volatile gradually released pest control agent. However, the use of these embodiments is not confined to pest control. There may be contained air freshener substance or scent releasing substances. Alternatively, the sachet may be filled with substances absorbing or absorbing gases or vapours from an environment, e.g. a drying agent or an agent for absorbing or otherwise rendering harmless phosphine gas prematurely released from phosphine releasing pest control agents while still contained in a package. Such compositions are known per se and require no description.

Referring now specifically to FIGS. 12 to 16 of the drawings, there is shown a specific embodiment of a belt-like applicator device in accordance with the invention wherein the high tensile strength of the sheet material is utilized in a particularly effective manner. This is a modification of the embodiment described with reference to FIGS. 2 to 5, but which could also be modified in the various manners described with reference to FIGS. 7 to 11, although this is not preferred. One of the main differences as compared with FIGS. 2 and 3, resides in the fact that this belt-like device, composed of a multitude of sachets interconnected by flexible hinge regions is of comparatively narrow configuration, there being provided but a single row of the sachets connected end to end, the individual sachet formations being comparatively narrow with two comparatively short sides adjoining the hinge regions and two by comparison much longer sides coinciding with the side edges 39 of the applicator. The reason is that this belt-like device generally indicated as 40 is not intended to be laid out flat on a supporting surface or on or near the top of the heaped commodities. The embodiment of FIGS. 12 to 16 is instead intended to be pushed by means of a rod-shaped long insertion probe down from the top as deeply as possible into heaped commodities such as grain.

Figure 12:
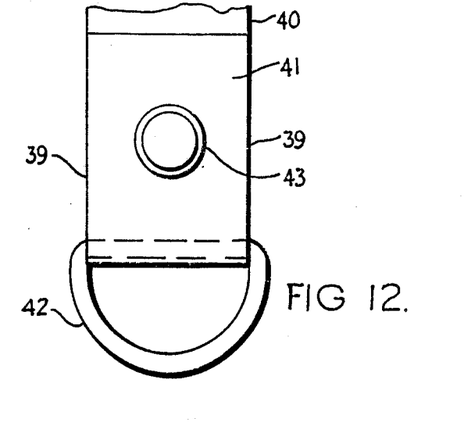
FIGS. 12 and 13 represent front and side elevations respectively of the bottom portion of a belt-like applicator device in accordance with the invention.
Figure 13:
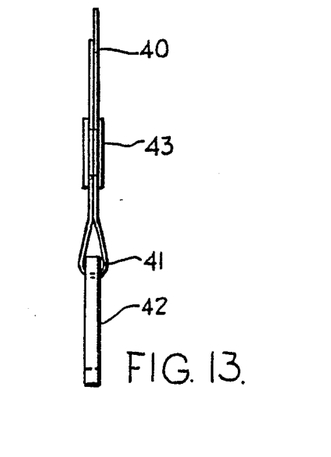
Figure 14:
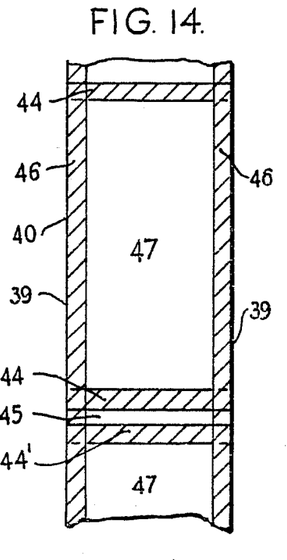
FIG. 14 represents a diagrammatic section parallel to the plane of FIG. 12 of an intermediate portion of the belt-like applicator.
Figures 15, 16:
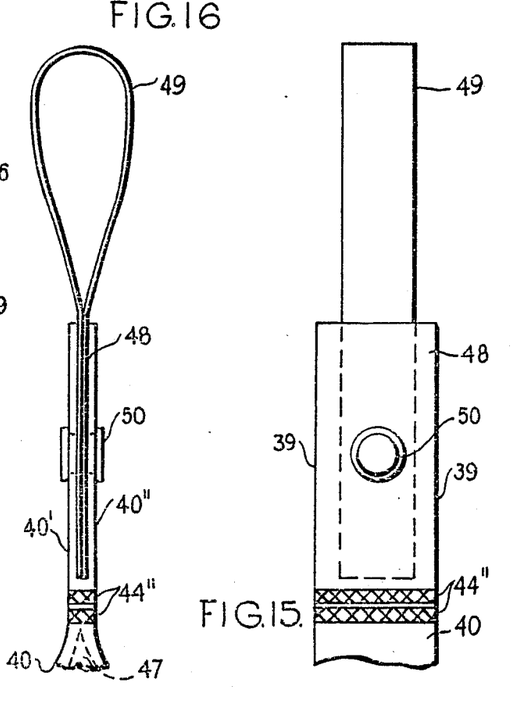
FIGS. 15 and 16 represent respectively front and side elevations similar to FIGS. 12 and 13, but of the top portion of the belt-like applicator device.

Past attempts to make such an applicator, using the fleece materials proposed in the prior art described above were not quite successful, because the fleece materials had insufficient tearing strength, and sometimes the sachets burst open even while still in the packaging container. Moreover, the comparative roughness of the prior art materials increased the frictional resistance when attempts to push the devices far down into grain and similar heaped commodities. These problems have been overcome in accordance with the present invention. In a typical example the total length of the belt 40 is 3080 mm. The belt 40 is basically composed of two layers 40' and 40" of the material described with reference to FIG. 1, welded lengthwise along the edges 39 by longitudinal welding seams 45 and 46 and subdivided into altogether 22 sachets 47 (in a typical example) by transverse pairs of welding seams 44 and 44' separated by a narrow gap 45, e.g. of about 5 mm.

In a typical embodiment the seams are 8 mm wide, the overall width of the belt is 70 mm and the length of each sachet, including seams is 140 mm. The two end sachets are kept empty, while the remainder are filled with pest control agent, in a typical example 25 grams each of the composition described in Example 1 further below.

At the bottom end (FIGS. 12 and 13) the empty end sachet of the belt is folded over at 41 to form a loop accommodating a strong stirrup device 42 made of steel. The loop 41 is closed by a strong eyelet device 43. Alternatively, but less preferably this may be done by welding, provided a welding bonding layer is provided as taught by the present invention.

At the top end of the device (FIGS. 15 and 16) in the region 48 a loop 49 of a strong plastics fabric is inserted between the layers 40' and 40" of the open-ended empty end sachet and fixed in place, strongly held between the two layers by a further eyelet 50. Once again (less preferably), welding may be resorted to.

The complete device is rolled up in the same manner as illustrated in FIG. 4 and sealed into a tin like tin 21 in FIG. 4. In practice there may be several, e.g. four belt devices accommodated in one such tin which is sealed gas- and moisture-tight for storage and shipping. Alternatively, the belt device may be folded concertina-like and packaged in the manner described with reference to FIG. 5.

Practical tests have shown that as a result of the smooth surface of the sheet material 40', 40" and the great strength of the device, it is possible to push down the belt by means of a rod-shaped probe, the end of which is hooked into the stirrup device 42, vertically down into the grain for the full length of the belt, and this ensures improved vertical gas distribution throughout the grain even in heaps of considerable heights, e.g. in shipholds. The loop 49 serves for the withdrawal of the applicator device after completion of the fumigation. Practical dosage rates for this device, range from 0.7 g to 28 g $PH_3$/ton of grain (i.e. 1 belt per 6–238 tons), preferably 3–11 g/ton (i.e. 1 belt per 15 to 55 tons), more particularly about 4 g $PH_3$ per ton (i.e. 1 belt per 42 tons), where 1 belt contains about 500 g of the preparation, containing about 167 g available $PH_3$.

EXAMPLE 1

Sachets as described with reference to FIG. 2 are each filled with 34 grams of a standard aluminium phosphide pest control powder mixture having the following composition: 70% technical AlP, 18.5% urea, 7.5% mixture of mono ammonium phosphate and sodium carbonate (1:1) and 4% aluminium stearate.

The dimensions of each sachet were approximately 100×90 mm.

For purposes of comparison prior art paper sachets of similar dimensions (100×80 mm) and containing the same amounts of the identical aluminium phosphide composition were prepared and also polyester fleece sachets, 100×90 mm (similarly according to the prior art), containing the same amount of powder having the identical composition.

These sachets were tested in a laboratory gas chamber having a volume of 0.5 m³, containing a dish filled with water for the maintenance of humidity and kept at a constant temperature of 20° C.

After various times the phosphine concentration in the gas chamber was measured. The results are apparent from the following table 1.

TABLE 1

| Time h | Paper Sachets | | | | Prior art polyester fleece sachets | | | | Sachets as per FIG. 2 | | |
|---|---|---|---|---|---|---|---|---|---|---|---|
| 1 | 50 | 40 | 60 | 50 | 50 | 50 | 60 | 50 | 40 | 50 | 4 |
| 2 | 130 | 160 | 160 | 150 | 150 | 200 | 170 | 170 | 90 | 100 | 90 |
| 4 | 450 | 550 | 500 | 500 | 500 | 400 | 450 | 450 | 210 | 300 | 230 |
| 6 | 600 | 850 | 800 | 35750 | 750 | 700 | 700 | 720 | 390 | 500 | 450 |
| 24 | 3 000 | 3 000 | 3 900 | 3 300 | 3 000 | 3 500 | 3 250 | 3 200 | 2 700 | 2 100 | 2 400 |
| 48 | 6 500 | 7 000 | 6 300 | 6 600 | 6 000 | 6 800 | 7 000 | 6 600 | 6 000 | 5 600 | 5 800 |
| 72 | 10 200 | 10 500 | 9 900 | 10 200 | 9 900 | 12 000 | 9 600 | 10 500 | 8 000 | 8 250 | 8 000 |
| 96 | — | — | — | — | — | — | — | — | 12 000 | — | 12 000 |
| 168 | 16 000 | 16 500 | 17 000 | 16 500 | 16 000 | 17 000 | 16 500 | 16 500 | 17 100 | 16 900 | 18 200 |

The residual contents of aluminium phosphide after the end of the experiment were as follows:

3.4% AlP and 3.2% AlP in the case of paper sachets and prior art polyester fleece sachets respectively and 2.6% AlP in the case of sachets according to the invention. This superior, more complete decomposition of the contents of sachets in accordance with the invention has been observed persistently. The reason for this superior result is unknown and an unexpected advantage of the invention.

It will also be seen that the rate of gas emission from the sachets according to the invention is more gradual, which is also a desirable effect for purposes of practical pest control.

EXAMPLE 2

Bag blankets made in accordance with FIG. 2 hereof and similar bag blankets made of the prior art polyester fleece were used side by side in the fumigation of a grain store containing 700 tons of wheat. The following table 2 represents typical phosphine concentration measurements at different fumigation exposure times, when concentration measurements are taken in direct contact with the blanket and at a level of 8 cm above the blanket in the grain, when applying the pest control agent at a rate of 27 grams available phosphine per ton of grain. (2.5 pockets per ton, each containing 34 g AlP mixture as in Example 1, altogether 18 bag blankets). This is a conventional dosage rate in some countries. The bag blankets were covered by about 20 cm of grain. The entire grain heap was covered with a gastight plastics foil.

The following table reflects the much more gradual release of phosphine from applicators according to the invention, whereby excessive concentrations at or close to the surface of the bag blankets are avoided and the distribution of phosphine gas throughout the grain is much more uniform.

TABLE 2

| | PH₃ - Concentrations in ppm | | | |
|---|---|---|---|---|
| | direct on blanket | | 8 cm above blanket in grain | |
| Time | Tyvek | prior art | Tyvek | prior art |
| 5 h | 17500 | 30000 | 800 | 11400 |
| 24 h | 15000 | 33000 | 1200 | 3300 |
| 48 h | 6000 | 13500 | 600 | 6000 |
| 72 h | 3300 | 15000 | 500 | 7500 |
| 5 days | 1200 | 2550 | 100 | 1350 |
| 6 days | 550 | 1140 | 100 | 880 |

EXAMPLE 3

Three types of sachets as described with reference to FIG. 10 of the drawings were prepared and tested. The sachets had the dimensions: 100×90 mm and the strips 35 of sheet material as described with reference to FIG. 1 had the following dimensions:

(a) 1 cm×9 cm,
(b) 2 cm×9 cm and
(c) 3 cm×9 cm.

Each sachet was filled with 24 g technical magnesium phosphide, impregnated with 3% solid paraffin. The sachets were exposed to moist air under the following conditions. The volume of the gas chamber was 0.5 m³. The chamber contained a dish of water to provide adequate humidity and the air was maintained at a constant temperature of 20° C. The magnesium phosphide was sufficient to produce a final gas concentration of 15 300 ppm after complete decomposition. However, the test was stopped after 144 hours. The rates of phosphine release to the gas chamber are apparent from table 3.

TABLE 3

| Time (h) | 1 cm strip (ppm) | 2 cm strip (ppm) | 3 cm strip (ppm) |
|---|---|---|---|
| 1 | 5 | 7.5 | 8 | 10 |
| 2 | 9 | 18 | 20 | 25 |
| 4 | 15 | 30 | 30 | 50 |
| 6 | 25 | 50 | 60 | 100 |
| 24 | 150 | 400 | 500 | 800 |
| 48 | 450 | 600 | 800 | 1200 |
| 72 | 600 | 900 | 1200 | 1800 |
| 144 | 2000 | 3900 | 4200 | 6500 |

It will be seen that the gas release was approximately proportional to the surface area of the gas pervious strip.

EXAMPLE 4

Sachets according to the invention as described with reference to FIG. 2, prior art paper sachets (with machine-sewn seams) and prior art polyester fleece sachets (all sachets being of the same dimensions) were each filled with 24 g technical magnesium phosphide impregnated with 3% solid paraffin as a hydrophobising agent.

The sachets were subjected to the following tests to determine their safety performance in the event of malpractices:

1. Drip experiment

Two sachets of each sample were so placed into a sheet metal through (200×150×50 mm) but they overlapped halfway. Water at 70° C. was dripped onto the sachets by means of a dropping funnel for 1 hour (1 drop per second). The experiment was conducted at an air temperature of 35° C.

2. Spray experiment

A sheet metal through containing sachets as used as in Experiment 1. 10 ml water was sprayed onto the sachets by means of a spraying flask. After 15 minutes a further 10 ml water was sprayed onto the sachets. This procedure was repeated for 1 hour.

3. Tin can experiment 3 sachets were placed into a 2 l tin can and 100 ml water at 70° C. were poured over the sachets. The can was left standing for 4 hours.

4. Bath experiment

The sachets were placed individually into a metal dish and so much water was poured thereover that the top of the sachet was at least 5 mm below the water surface. The dish was left standing for 4 hours.

5. Immersion test

An 800 ml glass beaker was filled with water. The test sachet was dipped for 5 to 10 seconds into the water, then withdrawn and shaken in water to remove the water. Thereafter the sachet was left lying for 4 hours.

6. Powder experiment 15 g of the powder mixture were introduced into a 150 ml glass beaker of narrow configuration. The beaker was heated in an airbath to a temperature of 50° C. When a temperature of 35° C. had been reached, 5 ml water were added through a pipette. The beaker was left standing for 1 hour.

All sachets ignited, except the sachets in accordance with the invention in their undamaged condition. In the powder experiment ignition took place, as was to be expected.

EXAMPLE 5

Grain was fumigated as in Example 2 but at a temperature which on average was about 10° C. higher and using a dosage rate of 68 g of the composition per ton of grains. In one experiment bag blankets according to the invention were used as in Example 2. In the comparative test conventional bag blankets were used wherein the composition was prepacked in paper sachets which were in turn enclosed in the conventional bag blankets. The concentrations of PH₃ (in ppm) measured in the grain at a distance of 15 cm from the bag blankets were as in Table 4.

TABLE 4

| | 5 h | 24 h | 48 h | 77 h | 92 h | 168 h |
|---|---|---|---|---|---|---|
| Tyvek blanket: | 2 400 | 12 000 | 12 000 | 12 000 | 15 000 | 1 800 |
| Paper sachets in convent. blanket | 6 000 | 18 600 | 24 000 | 21 000 | 15 900 | 1 100 |

It will be seen again that the phosphine generation according to the invention was much more evenly regulated, an effect which manifests itself in a much more even distribution of the gas throughout the grain over a prolonged period.

The claims filed herewith are to be considered a part of the present disclosure.

EXAMPLE 6

Comparison of physical characteristics with prior art:

The water vapor permeability of the fleeces used in accordance with the invention is selected in the range 300 to 1000 g/m²/24 h, preferably 500 to 750 g/m²/24 h. Commercially available qualities of spunbonded polyolefin fleece (Tyvek) which were found to be particularly suitable had water vapor permeabilities of 614–694 g/m$^2$/24 h (i.e. 600–700, nearest round numbers). These vapor permeabilities are not affected significantly by sprinkle-coating with EVA, average thickness 20–40 um. The water vapor permeabilities of the best prior art materials previously tested were twice as high, namely:

paper sachets: 1270 g/m$^2$/24 h
polyester wet fleece: 1251 g/m$^2$/24 h
polyolefin wet fleece: 1260 g/m$^2$/24 h The tear strengths of those suitable commercial polyolefin fleece materials having a thickness of 0.14 to 0.25 mm (average) range from 4.6 to 11.6N/mm in all directions, all but one of these materials being higher than 5. This is to be contrasted against the best prior art paper sachets, namely 4.1N/mm and the above prior art fleeces, namely 2–2.5N/mm.

Even more important are the onward-tearing (resistance to tear propagation) properties which are vastly superior in the case of the spunbonded polyolefin fleeces, as compared with the prior art materials.

What we claim is:

1. Applicator device for releasing at a controlled rate a gaseous pest-control medium to an environment comprising a container for holding a pest-control agent formed at least in part of a water vapor permeable plastic fleece material which is substantially impervious to pressure-less liquid water and has a water vapor permeability of not more than 1000 g/m$^2$/24 h.

2. Applicator device as claimed in claim 1, wherein the water vapor permeability is 300 to 1000 g/m$^2$/24 h.

3. Applicator device as claimed in claim 2, wherein the water vapor permeability is 500 to 750 g/m$^2$/24 h.

4. Applicator device as claimed in claim 1, wherein the fleece material is a spun-bonded synthetic paper fleece composed of heat and pressure bonded minute polyolefin fibers and has a tensile strength of not less than 4.6N/mm (ASTM D 823-60).

5. Applicator device as claimed in claim 4, containing a hydrolyzable metal phosphide.

6. A method of disinfesting commodities, buildings, packaging means, transport vehicles or shipholds or transport containers which comprises releasing phosphine gas there into from an applicator means as claimed in claim 5 and maintaining a pesticidal concentration of the released phosphine gas therein for a period effective to achieved disinfestation.

7. Applicator as claimed in claim 4, wherein the agent comprises at least one of aluminum phosphide, magnesium phosphide, calcium phosphide.

8. Applicator as claimed in claim 7, wherein the agent is technical aluminum phosphide or technical magnesium phosphide or a mixture of these phosphides, substantially free of additives or containing not more than a hydrophobising amount of a hydrophobising agent.

9. Applicator as claimed in claim 4, packed for storage and transport in a gas- and moisture-proof container.

10. Applicator as claimed in claim 1, wherein the fleece material is a heat weldable plastic sheet material comprising a spun-bonded, polyolefin sheet or fleece which is composed of heat and pressure bonded minute polyolefin fibers and which is vapor- and gas-pervious but impervious to liquid water and dust, naturally water-resistant and of high tensile and tear strength, coated at least in areas and on a side to be heat-welded with a thermoplastic highly porous heat welding bonding layer having a melting point or region sufficiently lower than that of the polyolefin fibers that conventional welding with heat and pressure results in a welding seam before the fibers reach their melting point so that the physical properties of the polyolefin fibers are substantially retained.

11. Applicator as claimed in claim 10, wherein the whole of one side thereof is thus coated and wherein the permeability to gas and moisture of the bonding layer is of an order of magnitude substantially higher than that of the polyolefin sheet.

12. Applicator as claimed in claim 10, wherein the difference in melting points or melting regions between the polyolefin fibers and the bonding layer is more than 20° C.

13. Applicator as claimed in claim 12, wherein the difference is from 30°–80° C.

14. Applicator as claimed in claim 12, wherein the difference is from 40° to 70° C.

15. Applicator as claimed in claim 12, wherein the difference is from 50° to 60° C.

16. Applicator as claimed in claim 10, wherein the polyolefin sheet is made from 100% high density polyethylene fibers by an integrated spinning and bonding process, formed by spinning very fine polyethylene fibers, each approximately 0.005 mm in diameter and laying the fibers down as a random network, and then bonding the fibers together with heat and pressure.

17. Applicator as claimed in claim 16, wherein the melting point or region of the polyolefin sheet is in the region of 135° C.

18. Applicator as claimed in claim 10, wherein the bonding layer is formed by sprinkling a bonding substance in powder form onto a supporting surface and fusing the substance onto that surface so that a high porosity is retained.

19. Applicator as claimed in claim 18, wherein the bonding substance is sprinkle-coated directly onto the polyolefin sheet followed by fusing at a temperature below the melting point or melting region of the fibers of the sheet.

20. Applicator as claimed in claim 18 wherein the bonding layer is applied by reverse coating.

21. Applicator as claimed in claim 10, wherein the amount of the bonding layer is 10 to 50 g/m$^2$.

22. Applicator as claimed in claim 10, wherein the amount of the bonding layer is 15 to 40 g/m$^2$.

23. Applicator as claimed in claim 10, wherein the bonding substance is ethylene vinyl acetate.

24. Applicator as claimed in claim 10, wherein the bonding substance is polyethylene.

25. Applicator as claimed in claim 1 for holding a gas-evolving or vapor-evolving pest control agent or substance, comprising sachets or pockets formed from and having seams produced by thermal welding sheet material comprising at least one layer or portion of a layer of the fleece material.

26. Applicator as claimed in claim 1 in the form of individual sachets or of bag blankets.

27. Applicator as claimed in claim 1, wherein the rate of gas or vapor-release therefrom is further determined by the available gas-pervious surface area of the sheet material per unit of composition enclosed in the applicator means.

28. Applicator as claimed in claim 27, wherein the available gas-pervious surface area is determined by the applicator being formed partly of the sheet material and the remainder of a different but compatible sheet material having little or no gas and vapor permeability.

29. Applicator as claimed in claim 1, wherein the available gas-pervious surface area is determined by coating a predetermined proportion of the gas-pervious surface area with a coating of little or no permeability.

30. An applicator as claimed in claim 1, wherein the volatile substance is an air freshener substance, scent, or insect or animal repellant.

31. An applicator means as claimed in claim 1 for holding a gas-evolving or vapour-evolving pest control agent or substance, comprising at least two sheets of sheet material bonded together by heat-welded welding seams to form a pocket or pockets for containing a substance from which vapors or gases are to be released, one sheet being composed of a spun-bonded, synthetic paper polyolefin first sheet or fleece which is composed of heat and pressure bonded minute polyolefin fibers and which is vapor- and gas-pervious but impervious to liquid water and use, naturally water-resistant and of high tensile and tear strength, and a second sheet composed of a thermoplastic foil or film weldable to the first sheet and having a melting point or region sufficiently lower than that of the first sheet to permit heat welding together the two sheets substantially without damage to the first sheet without a special bonding layer.

32. Applicator as claimed in claim 31 in the form of individual sachets or of bag blankets.

33. Applicator as claimed in claim 31 in which a sachet or pocket contains a metal phosphide pest control agent.

34. Applicator as claimed in claim 33, wherein the agent is based on aluminium phosphide, magnesium phosphide, calcium phosphide or more than one of these.

35. Applicator as claimed in claim 34, wherein the agent is technical aluminum phosphide or technical magnesium phosphide or a mixture of these phosphides, substantially free of additives or containing not more than a hydrophobising mount of a hydrophobising agent.

36. Applicator as claimed in claim 1, in the form of a belt device comprising a plurality of sachets or pockets connected end to end by hinge-like flexible regions of the belt, one end of the belt being folded over and fixed to form a loop which accommodates a stirrup device for the insertion of the belt into bulk commodities and the opposite end of the belt comprising a loop device for subsequent withdrawal of the belt.

* * * * *